US00RE42355E

(19) United States
(12) Reissued Patent
Heiniger

(10) Patent Number: US RE42,355 E
(45) Date of Reissued Patent: May 10, 2011

(54) DISPOSABLE INJECTOR CAP

(75) Inventor: Hanspeter Heiniger, Lotzwil (CH)

(73) Assignee: TecPharma Licensing AG, Burgdorf (CH)

(21) Appl. No.: 11/354,335

(22) Filed: Feb. 14, 2006

Related U.S. Patent Documents

Reissue of:
(64) Patent No.: 6,773,415
Issued: Aug. 10, 2004
Appl. No.: 10/232,967
Filed: Aug. 30, 2002

U.S. Applications:
(63) Continuation of application No. PCT/CH01/00104, filed on Feb. 16, 2001.

(30) Foreign Application Priority Data

Mar. 1, 2000 (DE) ..... 100 09 814

(51) Int. Cl.
*A61M 5/32* (2006.01)
*A61M 5/00* (2006.01)
*A61M 5/31* (2006.01)

(52) U.S. Cl. ..... 604/110; 604/198; 604/241

(58) Field of Classification Search ..... 604/198, 604/110, 241
See application file for complete search history.

(56) References Cited

U.S. PATENT DOCUMENTS

| | | | | |
|---|---|---|---|---|
| 4,894,055 | A | 1/1990 | Sudnak | |
| 4,915,701 | A * | 4/1990 | Halkyard | 604/198 |
| 5,405,362 | A * | 4/1995 | Kramer et al. | 607/5 |
| 5,429,612 | A * | 7/1995 | Berthier | 604/198 |
| 5,609,577 | A * | 3/1997 | Haber et al. | 604/110 |
| 5,681,291 | A * | 10/1997 | Galli | 604/198 |
| 5,688,241 | A * | 11/1997 | Asbaghi | 604/198 |
| 6,203,259 | B1 * | 3/2001 | Christensen | 410/100 |
| 6,391,003 | B1 * | 5/2002 | Lesch, Jr. | 604/110 |
| 6,855,129 | B2 | 2/2005 | Jensen et al. | |
| 6,960,194 | B2 * | 11/2005 | Hommann et al. | 604/198 |
| 7,534,229 | B2 * | 5/2009 | Hommann et al. | 604/187 |
| 2008/0177237 | A1 * | 7/2008 | Stonehouse et al. | 604/263 |

* cited by examiner

*Primary Examiner* — Kevin C Sirmons
*Assistant Examiner* — Andrew M Gilbert
(74) *Attorney, Agent, or Firm* — Dorsey & Whitney LLP; David E. Bruhn, Esq.

(57) ABSTRACT

An injector cap including a sleeve and a blocking means, wherein the sleeve is mounted slidably on a portion of an injection device, e.g., on an ampoule support, is forced by a pre-tensioning means into a first position in which it covers a cannula carried by the injection device, and can be slid against the pre-tensioning means into a second position in which the cannula emerges from the end of the sleeve, and wherein the blocking means non-detachably blocks the sleeve against sliding when it has been returned from the second position to the first position.

9 Claims, 4 Drawing Sheets

DISPOSABLE INJECTOR CAP

Matter enclosed in heavy brackets [ ] appears in the original patent but forms no part of this reissue specification; matter printed in italics indicates the additions made by reissue.

[PRIORITY CLAIM]

[This application is a Continuation Application of International Patent Application No. PCT/CH01/00104, filed on Feb. 16, 2001 now WO 01/64271 A1, which claims priority to German Application No. DE 100 09 814.2, filed on Mar. 1, 2000, both of which are hereby incorporated by reference.]

*CROSS-REFERENCE TO RELATED APPLICATIONS*

*The present application is a reissue application of and claims priority to U.S. Pat. No. 6,773,415 entitled "Disposable Injector Cap" issued on Apr. 10, 2004, application Ser. No. 10/232,967, filed Aug. 30, 2002, which is a continuation of International Application No. PCT/CH01/00104, filed Feb. 16, 2001, which claims priority to DE 100 09 814.2, filed Mar. 1, 2000, all of which are hereby incorporated by reference herein.*

BACKGROUND

The invention relates to an injector cap for an ampoule support. In particular, the invention relates to the field of so-called injection "pens", i.e., pen-like injectors or injection devices such as are used for hypodermally administrating medicines, for example for administering insulin for diabetics. The application claims the priority of German patent application No. 100 09 814, filed on Mar. 1, 2000 with the German Patent and Trademark Office.

Basically, injection pens comprise an ampoule support on which a cannula support comprising a cannula is arranged on a facing side. A cap is fastened over the cannula or needle, said cap in its basic state completely hiding the cannula or needle. From this position, the cap can be retracted in the direction of the ampoule support, wherein the cannula emerges from a hole formed on the front facing side of the cap. It is therefore possible to place the pen on the skin, press on it such that the cap slides backwards against a spring force, administer the injection and remove the pen again, wherein the spring force ensures that the cap is returned to its initial position and the needle is hidden again. In this way, a user can administer the injection without ever even seeing the needle, which is particularly advantageous when patients who have phobias or aversions to needles are reliant on such treatments. Moreover, the cap protects the cannula from contamination.

A "pen" is known from U.S. Pat. No. 5,609,577 in which the cap can only be retracted once a holding mechanism is twisted up against a spring force. A disadvantage of the pen disclosed in the '577 patent and other conventional injectors is that the cannula can easily be exposed again after the injector has been used. This creates the danger that a cannula which is no longer sterile is used a second time and so causes inflection. Furthermore, such an exposed cannula can cause injury and transmit diseases, which in the age of Aids can be life-threatening.

SUMMARY

It is therefore the object of the present invention to provide an injector cap which does not exhibit the above disadvantages. In particular, the intention is to simply but reliably prevent the possibility of the cannula of an injector provided with the cap being used or exposed again after having been used once.

This object is addressed in accordance with the present invention by providing an injector cap for an ampoule support, said cap comprising a sliding sleeve slidably mounted on said ampoule support, wherein the sliding sleeve is pressed by a pre-tensioning means into a first position in which it covers a cannula, and wherein the sliding sleeve can be slid against the pre-tensioning into a second position in which the cannula emerges from the front facing end of the sliding sleeve, wherein a blocking means is provided which non-detachably blocks the sliding sleeve against sliding further when it has been returned from the second position to the first position. The invention further relates to an injector comprising an ampoule support of an injector cap in accordance with the invention.

In one embodiment, the present invention comprises an injector cap comprising a sleeve and a lock, wherein the sleeve is mounted slidably on a portion of an injection device, e.g., on an ampoule support, is forced by a pre-tensioning means into a first position in which it covers a cannula carried by the injection device, and can be slid against the pre-tensioning means into a second position in which the cannula emerges from the end of the sleeve, and wherein the lock non-releaseably locks the sleeve against sliding when it has been returned from the second position to the first position.

An advantage of the injector cap in accordance with the invention is that an injector equipped with said cap cannot be used again once it has been used once. Furthermore, it is not possible to expose again a cannula which has already been used once, such that the danger of injury and thus also the danger of infection are practically completely removed.

In one embodiment, the blocking means comprises locking means, by means of which the sliding sleeve is locked relative to a fixed part of the ampoule support, once it has returned to the first position. In particular, the blocking means can comprise a locking ring which is slidably mounted in the sliding sleeve and locks in behind a locking protrusion of a cannula support fastened to the ampoule support, when the sliding sleeve is slid into the second position.

In an embodiment of the latter variant, the locking ring comprises locking clips arranged circumferentially and converging inwards, which lock in behind the locking protrusion.

There exists the possibility of additionally providing spacer clips which the sliding sleeve pushes against, once the sliding sleeve has returned to the first position, and preferably via elastic stays on the sliding sleeve.

In accordance with an embodiment of the latter variant, the sliding sleeve comprises a stopper for the spacer clips of the locking ring which, when the sliding sleeve is transferred from the first position to the second position, slides the locking ring over the cannula support until the locking clips lock in behind the locking protrusion of the cannula support.

The invention further relates to an injector comprising an ampoule support and an injector cap designed in accordance with one or more of the embodiments described above. In one embodiment in this respect, the injector cap or cannula support is attached to the ampoule support via a thread means. If these components are screwed on, there no longer exists the danger of the injector cap latching via the blocking mechanism even when it is attached to the ampoule support for the first time, thus preventing its use.

DETAILED DESCRIPTION

Figure 1:
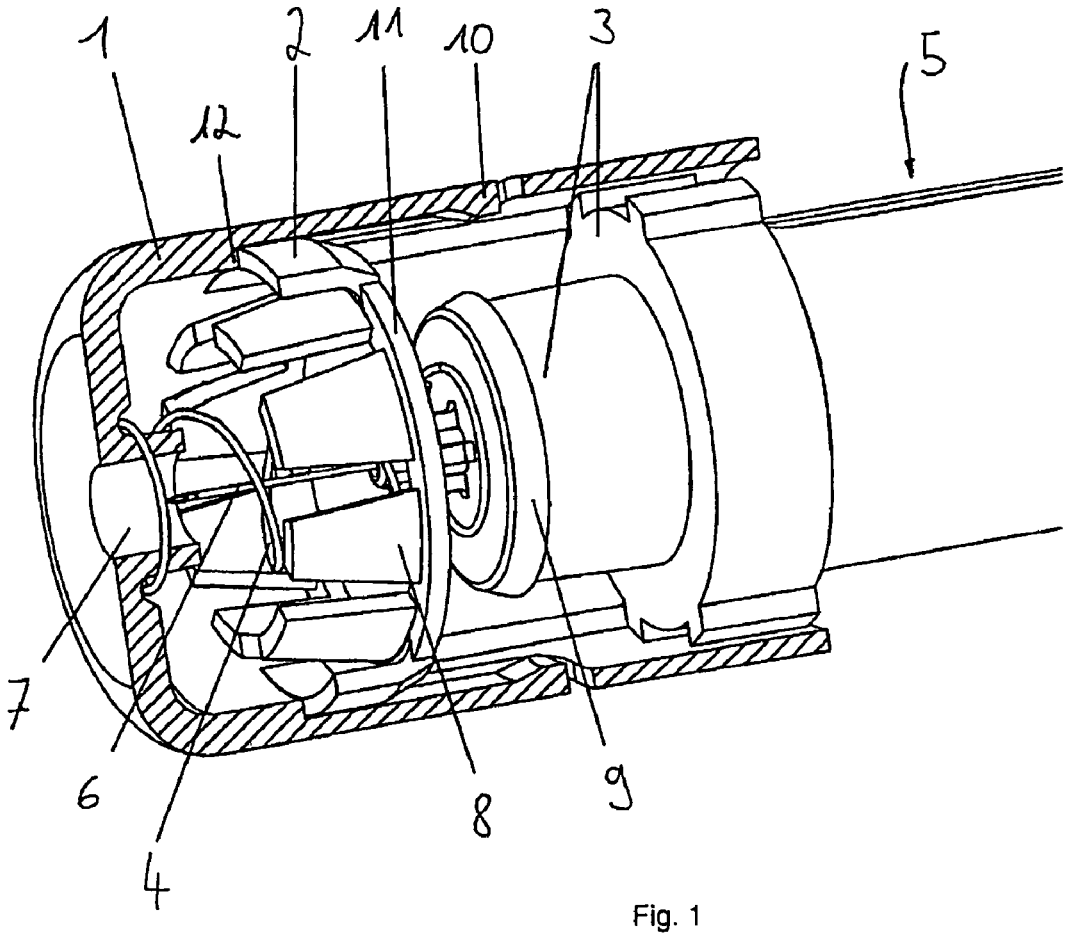
FIG. 1 is a perspective representation of a cut-away injector cap in accordance with the invention, in its initial state on the ampoule support.

The design of an injector cap in accordance with the invention and attaching it to an ampoule support will now be illustrated first, with reference to FIG. 1.

In the figures, the ampoule support is indicated by the reference numeral 5. A cannula support 3 is placed at its front facing end, said cannula support in turn keeping the cannula 6 protruding towards the front both at its facing side and centrally. The cannula support 3 comprises a locking protrusion 9, running in a circle, at the front end of its circular cylindrical section, said locking protrusion forming a heel at its end facing the ampoule support 5, and tapering towards the other side.

The components described above are those which are fixed in their positions.

Figure 2:
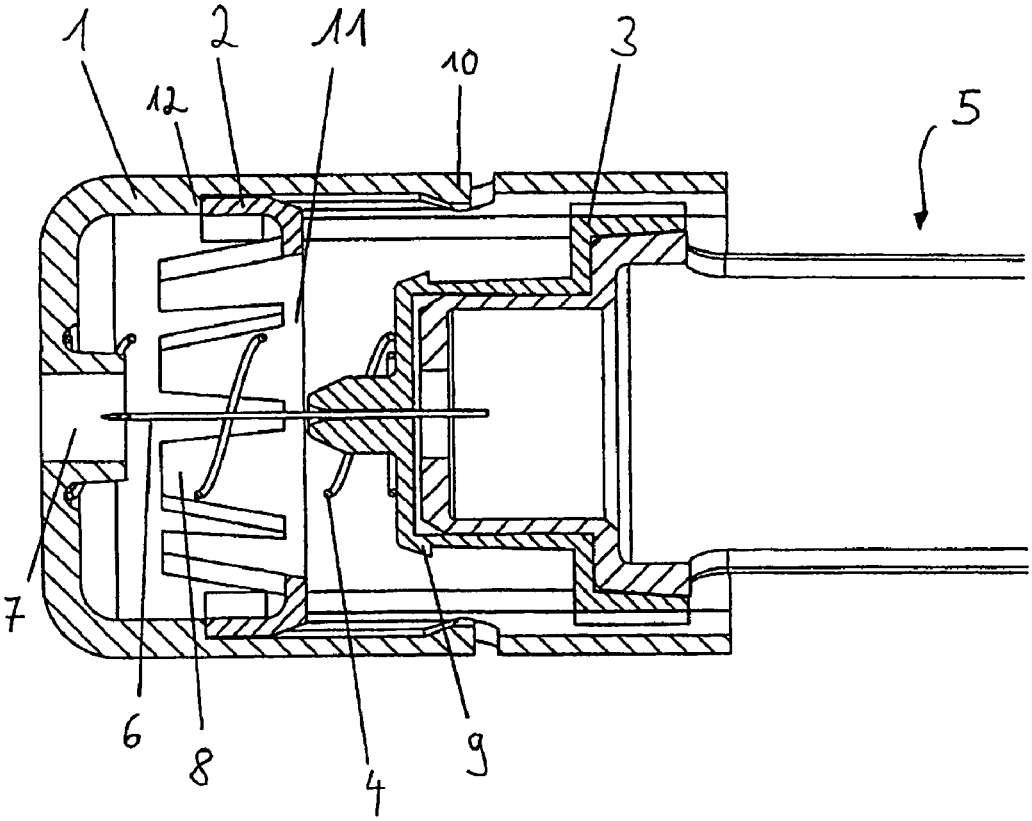
FIG. 2 is a longitudinal section of the arrangement shown in FIG. 1, in its initial state.

The cut-away sliding sleeve 1 is shown in FIGS. 1 and 2, mounted slidably and like a cap. As with the components described herein below, this sleeve 1 is one of the movable components of the injector cap.

In the initial state shown in FIGS. 1 and 2, the injector is ready to administer an injection. To this end, the sliding sleeve 1 is situated in a first position in which its facing side exhibits its greatest distance from the ampoule support 5. In this state, the cannula 6 is completely hidden within the sliding sleeve 1. The sliding sleeve 1 is held in the position in which it is shown in FIGS. 1 and 2 by a spring 4 between the facing end of the cannula support 3 and inner attachment (not shown) at the facing end of the sliding sleeve 1. A circular opening 7 is provided on the front facing wall of the sliding sleeve 1, to provide the cannula 6 with a way of emerging.

A locking ring, indicated at 11, is mounted slidably in a guide on the inside of the sliding sleeve 1. In the initial state shown in FIGS. 1 and 2, the locking ring 11 comprises inner locking clips 8, arranged circumferentially and forwards and converging inwards, as well as two spacer clips 2 likewise extending forwards and further outwards. The locking ring 11 abuts the stopper 12 of the sliding sleeve 1 via its spacer clips 2, i.e., via its front facing edge. The stopper 12 forms the front end of the guide for the locking ring 11, said guide being worked out of the inside of the sliding sleeve 1 over a particular length.

In this area, the sliding sleeve 1 also comprises two opposing stays 10, exposed from the surrounding material, which at their free end form a heel protruding obliquely inwards. The stays 10 can be elastically deformed in the radial direction.

Figure 3:
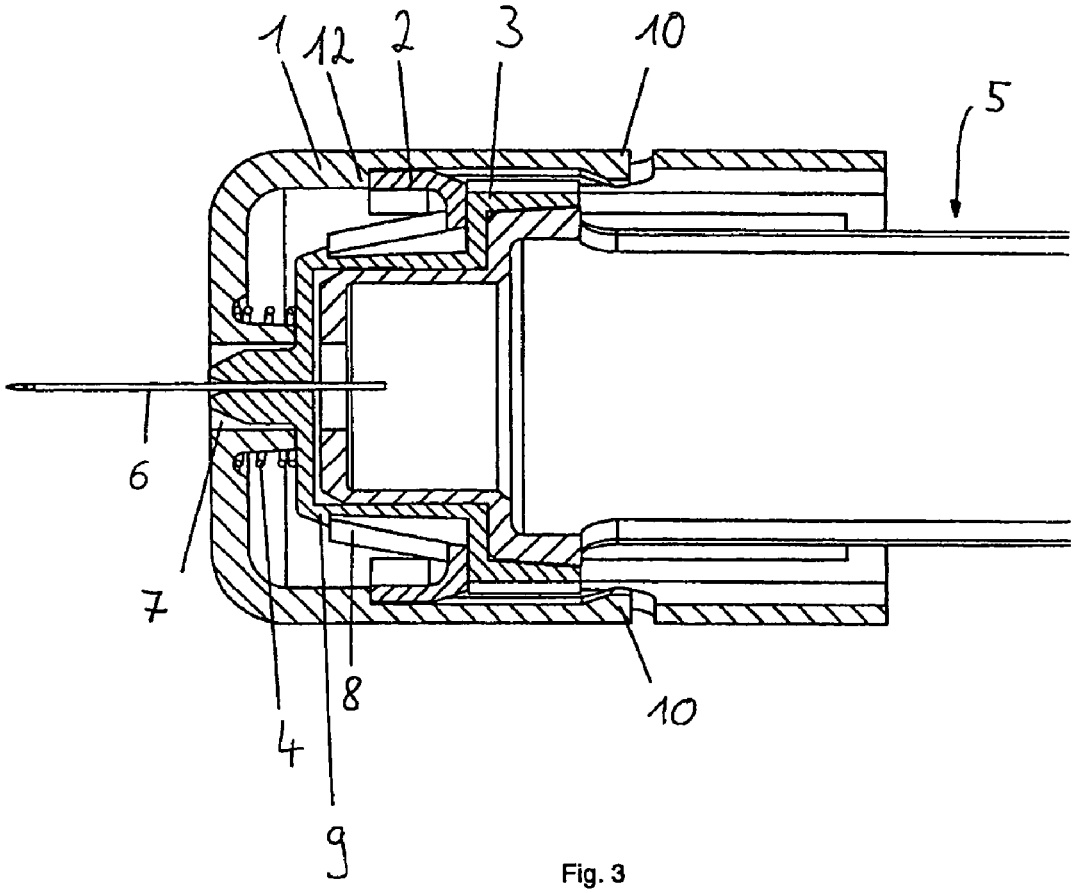
FIG. 3 is a longitudinal section through the injector arrangement in accordance with the invention, comprising the injector cap in its fully retracted state (second position)
Figure 4:
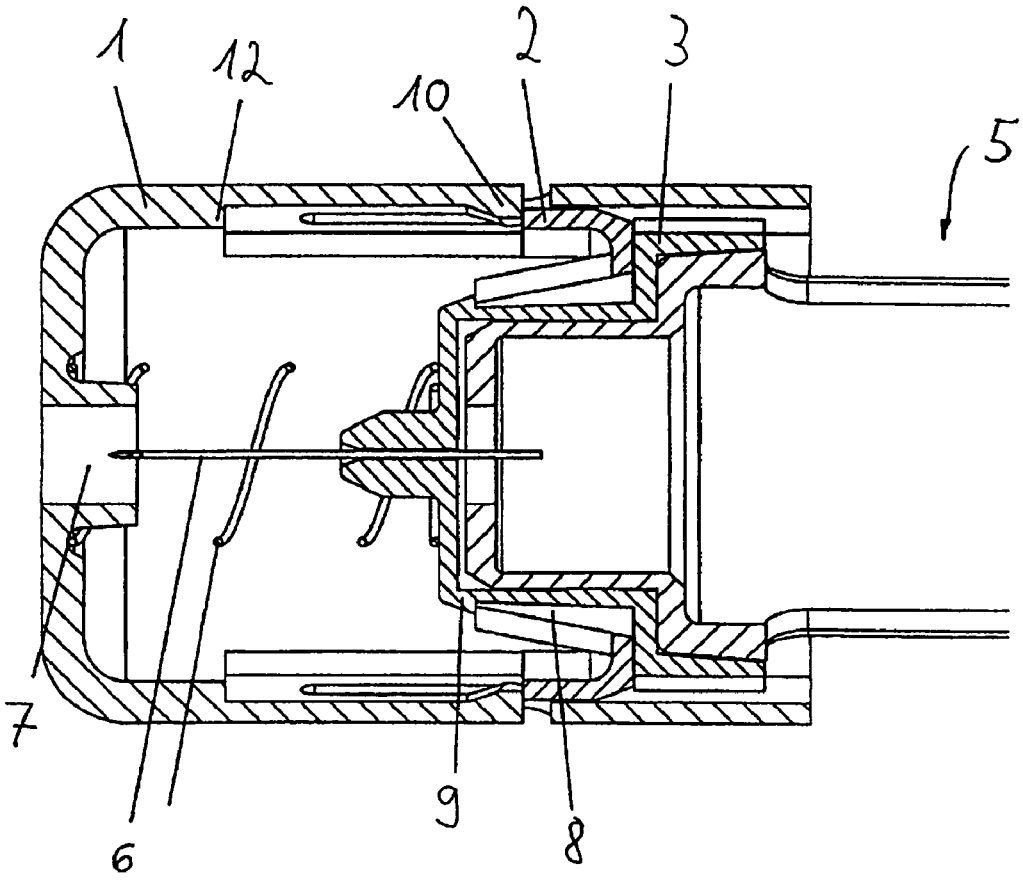
FIG. 4 depicts an injector arrangement in accordance with the invention, in a longitudinal section, according to its use in accordance with the regulations, the injector cap being retracted into its initial state and blocked against sliding further.

Proceeding from the state shown in FIGS. 1 and 2, it can be shown by way of the representations in FIGS. 3 and 4 how the injector cap in accordance with the present invention functions.

If a dose of medicine is to be administered by means of the injector, then said injector is placed on the skin of a patient at the front facing side of the sliding sleeve 1.

The ampoule support 5 is then slid forwards, such that the sliding sleeve 1 slides backwards relative to the ampoule support 5 and against the force of the spring 4, until the cannula support 3 abuts the inner attachment at its front facing end, said attachment surrounding the opening 7 and being enclosed by the spring 4. This state is shown in FIG. 3.

Activating the device as described above does not affect the position of the locking ring 11 comprising the clips 8 and clips 2 relative to the sliding sleeve 1, i.e., the spacer clips 2 are still pressing against the stopper 12. What does change, however, is the position of the locking ring 11 relative to the cannula support 3; the cannula support 3 is slid, together with the ampoule support 5, forwards into the locking ring 11, through the locking clips 8. As they pass through the locking protrusion 9, this first pushes the locking clips 8 outwards, somewhat elastically, and they then latch in behind the locking protrusion 9, fixing the locking ring 11 with respect to the cannula support 3.

In this state, the cannula 6 has traveled far out of the opening 7, and the injection can be administered.

After the injection has been administered, the spring 4 causes the sliding sleeve 1 to be slid back away from the cannula support 3, as depicted in FIG. 4.

Since, as shown in FIG. 3 and already mentioned above, the locking ring 11 is then fixed behind the locking protrusion 9 on the cannula support 3 by the locking clips 8, it also remains fixed when the sliding sleeve 1 is brought forward again, i.e., the sliding sleeve 1 moves forward again without slaving the locking ring 11. As the sliding sleeve 1 thus moves forward, the stays 10 then slide along the outer circumference of the spacer clips 2 and are briefly, elastically pressed outwards as the rear heel passes over the spacer clips 2, before they latch back inwards beyond the front end of the spacer clips 2 with their rear facing end. After this latching back, the stays 10 are in the position shown in FIG. 4, i.e., they abut the front area of the spacer clips 2 with their facing side. This locks or prevents the sliding sleeve 1 from sliding back again relative to the cannula support 3 or the ampoule support 5.

In the state depicted in FIG. 4, once the medicine dose has been administered once, the sliding sleeve 1 is therefore blocked against sliding further and again completely covers the cannula 6 against the environment. In this way, using the injector again is positively prevented. The possibility of injury or infection from the needle is likewise prevented.

The locking and/or blocking means of an injector cap in accordance with the invention are all substantially situated in the interior of the cap or have their functional parts facing the interior, such that repeated use—which in accordance with health care standards and regulations is not supposed to happen—can only be achieved by extensively manipulating it, which would probably lead to the injector or injector cap being destroyed.

In the foregoing description embodiments of the invention have been presented for the purpose of illustration and description. It is not intended to be exhaustive or to limit the invention to the precise form disclosed. Obvious modifications or variations are possible in light of the above teachings. The embodiment was chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. An injector cap for an ampoule support, comprising:

a sliding sleeve mounted slidably on said ampoule support, wherein said sliding sleeve is *initially* forced by a pre-tensioning means into a first position in which the sliding sleeve covers a cannula, and wherein said sliding sleeve can be slid against the pre-tensioning means into a second position in which said cannula emerges from a front facing end of said sliding sleeve *such that medication may be administered and wherein the sliding sleeve returns to the first position after the medication is administered*; and a blocking means for non-detachably blocking the sliding sleeve against sliding again into the second position when the sliding sleeve has been returned from the second position to the first position, *wherein an inner surface of the sliding sleeve is provided with at least two protrusions protruding radially inwardly from the inner surface of the sliding sleeve, and* wherein the blocking means includes a locking ring disposed inside [and proximate at a front end of] the sliding sleeve when the sliding sleeve is *initially* forced by the pre-tensioning means into the first position, and the locking ring is [engageably] moved along [with] the cannula [back] to [the first] *a locking* position, *wherein the locking ring includes at least two locking elements protruding radially outward, and, upon return of the sliding sleeve to the first position, the at least two protrusions on the sliding sleeve abut the at least two locking elements on the locking ring* to [help] block the sliding sleeve against sliding again into the second position when the sliding sleeve has been returned from the second position to the first position.

2. The injector cap as set forth in claim 1, wherein said blocking means [comprises locking means for locking] *locks* said sliding sleeve relative to a fixed part of said ampoule support once the sliding sleeve has returned to said first position.

3. The injector cap as set forth in claim 1, wherein the locking ring is slidably mounted in said sliding sleeve and locks in behind a locking protrusion of a cannula support fastened to said ampoule support when said sliding sleeve is slid into said second position.

4. The injector cap as set forth in claim 3, wherein said locking ring comprises locking clips arranged circumferentially and converging inwards, said locking clips locking in behind said locking protrusion.

5. The injector cap as set forth in claim 3, wherein said [locking ring] *at least two locking elements* [comprises] *comprise* spacer clips[which said sliding sleeve pushes against, via elastic stays, once said sliding sleeve has returned to said first position].

6. The injector cap as set forth in claim 5, wherein said sliding sleeve comprises a stopper for said spacer clips of said locking ring which, when said sliding sleeve is transferred from said first position to said second position, slides said locking ring over said cannula support until said locking clips lock in behind said locking protrusion.

7. An injector, comprising:

an ampoule support; and an injector cap, said injector cap comprising:

a sliding sleeve mounted slidably on said ampoule support, wherein said sliding sleeve is *initially* forced by a pre-tensioning means into a first position in which the sliding sleeve covers a cannula, and wherein said sliding sleeve can be slid against the pre-tensioning into a second position in which said cannula emerges from a front facing end of said sliding sleeve *such that medication may be administered and wherein the sliding sleeve returns to the first position after the medication is administered*; and a blocking means for non-detachably blocking the sliding sleeve against sliding again into the second position when the sliding sleeve has been returned from the second position to the first position, *wherein an inner surface of the sliding sleeve is provided with at least two protrusions protruding radially inwardly from the inner surface of the sliding sleeve, and* wherein the blocking means includes a locking ring disposed inside [and proximate at a front end of] the sliding sleeve when the sliding sleeve is *initially* forced by the pre-tensioning means into the first position, and the locking ring is [engageably] moved along [with] the cannula [back] to [the first] *a locking* position, *wherein the locking ring includes at least two locking elements protruding radially outward, and, upon return of the sliding sleeve to the first position, the at least two protrusions on the sliding sleeve abut the at least two locking elements on the locking ring* to [help] block the sliding sleeve against sliding again into the second position when the sliding sleeve has been returned from the second position to the first position.

8. The injector as set forth in claim 7, wherein at least one of said injector cap and cannula support is attached to said ampoule support via a thread means.

9. An injector cap for use on *an* injection device, comprising:

a *sliding* sleeve movably mounted on a portion of the injection device, wherein the *sliding* sleeve is *initially* forced by a pre-tensioning member into a first position covering a needle carried by the injection device and can be moved against the pre-tensioning member into a second position in which the needle emerges from the *sliding* sleeve *such that medication may be administered and wherein the sliding sleeve returns to the first position after the medication is administered*; and a lock which non-releaseably locks the *sliding* sleeve against moving back to the second position when the sliding sleeve has been returned from the second position to the first position, *wherein an inner surface of the sliding sleeve is provided with at least two protrusions protruding radially inwardly from the inner surface of the sliding sleeve, and* wherein the lock includes a locking ring disposed inside [and proximate at a front end of] the sliding sleeve when the sliding sleeve is *initially* forced by the pre-tensioning member into the first position, and the locking ring is [engageably] moved along [with] the needle [back] to [the first] *a locking* position, *wherein the locking ring includes at least two locking elements protruding radially outward, and, upon return of the sliding sleeve to the first position, the at least two protrusions on the sliding sleeve abut the at least two locking elements on the locking ring* to [help] block the sliding sleeve against sliding again into the second position when the sliding sleeve has been returned from the second position to the first position.

[10. The injector cap according to claim 9, wherein the sleeve slides.]

* * * * *